(12) United States Patent
Yamaguchi et al.

(10) Patent No.: US 7,705,174 B2
(45) Date of Patent: Apr. 27, 2010

(54) CONDENSED POLYCYCLIC π-CONJUGATED ORGANIC MATERIAL, INTERMEDIATE PRODUCT THEREFOR, AND METHOD OF MANUFACTURING CONDENSED POLYCYCLIC π-CONJUGATED ORGANIC MATERIAL

(75) Inventors: Shigehiro Yamaguchi, Nagoya (JP); Caihong Xu, Beijing (CN); Kohei Tamao, Kyoto (JP)

(73) Assignee: Japan Science and Technology Agency, Tokyo (JP)

( * ) Notice: Subject to any disclaimer, the term of this patent is extended or adjusted under 35 U.S.C. 154(b) by 1105 days.

(21) Appl. No.: 10/525,221

(22) PCT Filed: Aug. 20, 2003

(86) PCT No.: PCT/JP03/10538

§ 371 (c)(1),
(2), (4) Date: Jan. 18, 2006

(87) PCT Pub. No.: WO2004/018488

PCT Pub. Date: Mar. 4, 2004

(65) Prior Publication Data

US 2006/0100433 A1    May 11, 2006

(30) Foreign Application Priority Data

Aug. 23, 2002  (JP) .............................. 2002-244315

(51) Int. Cl.
*C07F 7/08* (2006.01)
(52) U.S. Cl. ...................................... 556/406
(58) Field of Classification Search .................. 556/406
See application file for complete search history.

(56) References Cited

OTHER PUBLICATIONS

Ma et al, "Design and synthesis of novel blue-light-emitting photoluminescent monomers and polymers" Polymer Preprints, 1997, vol. 38, No. 2, pp. 249-250.*
Ioerg "N02-06: Molecular Weight of RESOMER" Boehringer Ingelheim Memo, Apr. 7, 2006, pp. 1-6.*
"Trans-Cis Photoisomerization of the Stilbenes and a Reexamination of the Positional Dependence of the Heavy-Atom Effect", Jack Saltiel et al., Journal of the American Chemical Society / 101:11, May 23, 1979, pp. 2982-2996.
"Tests of the Singlet Mechanism for *cis-trans* Photoisomerization of the Stilbenes", Jack Saltiel et al., Journal of the American Chemical Society / 90:17, Aug. 14, 1968, pp. 4759-4760.
"Structural Optimization of 2,5-Diarylsiloles as Excellent Electron-Transporting Materials for Organic Electroluminescent Devices", Manabu Uchida et al., Chem. Mater., vol. 13, No. 8, 2001, pp. 2680-2683.
"Synthesis and Chemistry of a Trisiladibenzocyclodiyne", Mike Serby et al. (*same as XXXIIIrd Symposium on Organosilison Chemistry listed on pp. 3 and 17-18 of the Specification as filed on Feb. 22, 2005).
MA Zhongxin et al., "Design and synthesis of novel blue-light-emitting photoluminescent monomers and polymers, polymer preprints" (American Chemical Society, Division of Polymer Chemistry), 1997, vol. 38, No. 2, pp. 249 to 250, schemes 1,2.
Kowalik, Janusz et al., "Diphenylacetylene and the LICKOR superbase: o, o'-Dimetalation and Reaction with Electrophiles. A Convenient Synthesis of o, o'-Disubstituted Diphenylacetylenes," Journal of Organic Chemisty, 2001, vol. 66, No. 9, pp. 3229 to 3231, scheme 1, table 1.
Dawkins, John V., "Size Exclusion Chromatography," Comprehensive Polymer Science: The Synthesis, Characterization, Reactions & Applications of Polymers, vol. 1, Polymer Characterization, 1989, pp. 231-259.

* cited by examiner

*Primary Examiner*—Joseph R Kosack
(74) *Attorney, Agent, or Firm*—Harness, Dickey & Pierce, P.L.C.

(57) ABSTRACT

The invention provides condensed polycyclic π-conjugated organic materials and manufacturing methods for the materials. A metal reducing agent is reacted with a straight-chain, triple bond-containing hydrocarbon (aryl acetylene compound, phenyl acetylene compound), the hydrocarbon being a benzene ring with an organic silicon as a substituent, so as to allow an intramolecular reductive cyclization reaction to proceed between the silicon and the triple-bond carbon. The reaction produces condensed polycyclic π-conjugated organic materials of the invention. The invention provides light-emitting materials applicable for organic electroluminescent devices, condensed polycyclic π-conjugated organic materials applicable for charge transport materials, their intermediate products, and a manufacture method for condensed polycyclic π-conjugated organic materials.

4 Claims, No Drawings

CONDENSED POLYCYCLIC π-CONJUGATED ORGANIC MATERIAL, INTERMEDIATE PRODUCT THEREFOR, AND METHOD OF MANUFACTURING CONDENSED POLYCYCLIC π-CONJUGATED ORGANIC MATERIAL

TECHNICAL FIELD

The present invention relates to condensed polycyclic π-conjugated organic materials applicable to light-emitting materials for use in organic electroluminescent (EL) and like devices, as well as applicable to charge transport materials. The invention also relates to intermediate products and manufacturing methods for the condensed polycyclic π-conjugated organic materials.

BACKGROUND ART

Various studies have been conducted on displays based on electroluminescent devices to exploit their low power consumption, slimness, and other advantages. Especially, EL displays have been extensively studied because they are easy to decrease in weight and increase in screen size.

Focus of these studies has been upon the development of organic materials which emit light at blue wavelengths, one of the three primary colors, as well as upon the development of organic materials with a capability to transport charges (holes, electrons, etc.). The latter organic materials can possibly be semiconductors or superconductors. The studies have been targeted at both low molecular weight compounds and high molecular weight compounds.

Still, we know only a limited number of organic materials with either excellent color purity and light emitting efficiency or excellent electric charge (carrier) mobility and carrier injection. This challenging issue currently faces our field of study.

Constructing molecules with a highly planar π-conjugated structure is said to be an effective approach to the designing of an organic material with high light emitting efficiency and charge transport capability. A typical, well-known example is given by J. Saltiel, A. Marinari, D. W. L. Chang, J. C. Mitchener, and E. D. Megarity, in J. Am. Chem. Soc., Vol. 101, p. 2982 (1979) and also by J. Saltiel, O. C. Zafiriou, E. D. Megarity, and A. A. Lamola, in J. Am. Chem. Soc., Vol. 90, p. 4759 (1968). Trans-stilbene (see the formula below) in a solution exhibits no higher than a fluorescent quantum yield of 0.05 at room temperature. In contrast, 5,10-dihydroindeno[2,1-a]indene, derived from trans-stilbene by crosslinking its structure with a methylene chain (see the formula below), exhibits a fluorescent quantum yield of close to 1 at room temperature.

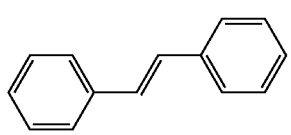

trans-stilbene

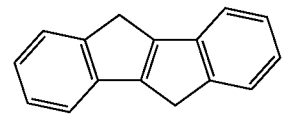

5,10-dihydroindeno[2,1-a]indene

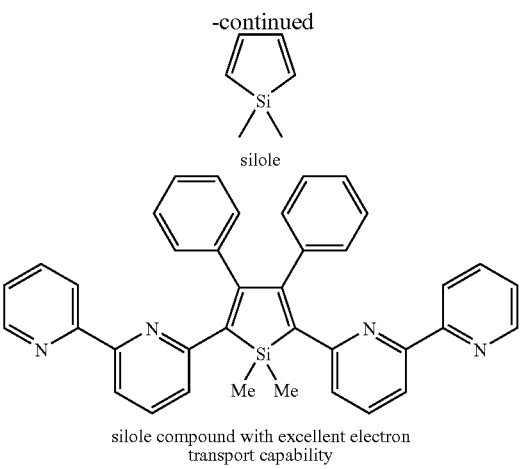

silole silole compound with excellent electron transport capability

We have thought of using a silicon substituent instead of the methylene chain. High light emitting efficiency is obtained with the silicon similarly to the case of the methylene chain. The use of silicon also results in imparting good charge transport capability because of substituent effects of the silicon.

This is because a π-conjugated compound containing silacyclopentadiene (i.e., silole) rings exhibits high electron mobility and acts as a material with an excellent electron transport property. The silole is a silicon analogue of a cyclopentadiene (see the formula above). These facts are well known. See M. Uchida, T. Izumizawa, T. Nakano, S. Yamaguchi, K. Tamao, K. Furukawa, Chem. Mater., Vol. 13, p. 268 (2001).

An example of such a compound is 5,5,10,10-tetramethyl-5,10-disila-5,10-dihydroindeno[2,1-a]indene. The compound is known to be prepared through a reaction shown in formula (I). See M. Serby, S. Ijadi-Maghsoodi, and T. J. Barton, XXXIIIrd Symposium on Organosilicon Chemistry, Abstract No. PA-35, Apr. 6-8, 2000, Saginaw, Mich., USA.

Reaction formula (I)

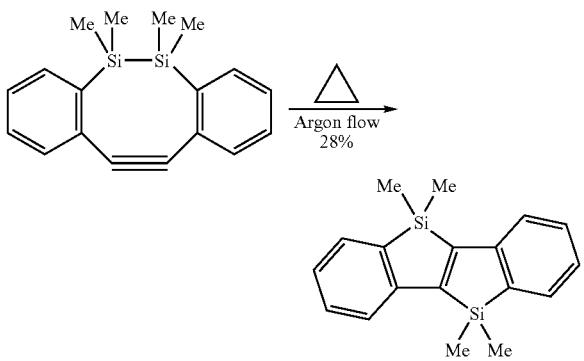

The synthesis of the compound, however, involves special thermal decomposition reactions at high temperatures as will be illustrated later in a reaction formula. The reactions present serious constraints in the synthesis. The reaction is: (i) not suited to mass-volume synthesis, (ii) not suited to the synthesis of derivatives containing functional groups which are essential to the synthesis of polymers, and (iii) not applicable to the synthesis of condensed polycyclic compounds.

To eliminate these serious constraints, we have worked on the development of a synthesis based on a new concept, which has led to the completion of the present invention.

DISCLOSURE OF INVENTION

We have diligently worked to address the issue and as a result, discovered novel compounds containing a structure of formula (1) below, as well as their manufacturing methods. We have also discovered novel polymer compounds which contain the novel compound as repeating units and weigh $10^3$ to $10^8$ in number average polystyrene-equivalent molecular weight, as well as their manufacturing methods. We have further discovered that these compounds show a good light emitting property, a high charge transport capability, and other advantages, which has led to the completion of the invention. It should be noted that the term "number average polystyrene-equivalent molecular weight" is intended to mean the number average molecular weight as determined by gel permeation chromatography (GPC) using a calibration curve obtained with use of a monodisperse polystyrene. The number average molecular weight is the ordinary arithmetic mean, or average, of the molecular weights of individual macromolecules, determined by measuring the molecular weight of n polymer molecules, summing the weights, and dividing by n.

A condensed polycyclic π-conjugated material in accordance with the present invention, to address the issue, is characterized in that the material contains a compound of formula (1):

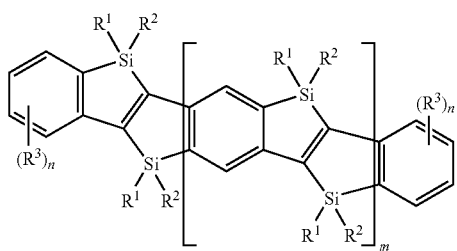

(1)

where each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^3$ is a hydrogen atom, an alkyl group, an alkylthio group, an arylalkyl group, an arylthio group, an arylalkylthio group, an arylalkenyl group, an arylalkynyl group, an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; m is from 1 to 50; and n is from 0 to 4.

According to the arrangement, the material is a planar, condensed polycyclic π-conjugated organic material prepared by condensing a benzene ring and a silole ring. The material therefore shows a good light emitting property, a high charge transport capability, and other advantages. The material is effective when used as an organic light-emitting material in EL displys, organic charge transport material, etc.

The definition, "m is from 1 to 50," means that m may be set to any one of integers from 1 to 50. The definition, "n is from 0 to 4," means that n may be set to any one of integers from 0 to 4 and that when n is from 0 to 3, there are as many substituting hydrogen atoms in the benzene ring as a difference between n and 4.

Additional objects, advantages and novel features of the invention will be set forth in part in the description which follows, and in part will become apparent to those skilled in the art upon examination of the following or may be learned by practice of the invention.

BEST MODE FOR CARRYING OUT THE INVENTION

The following will describe an embodiment of the present invention.

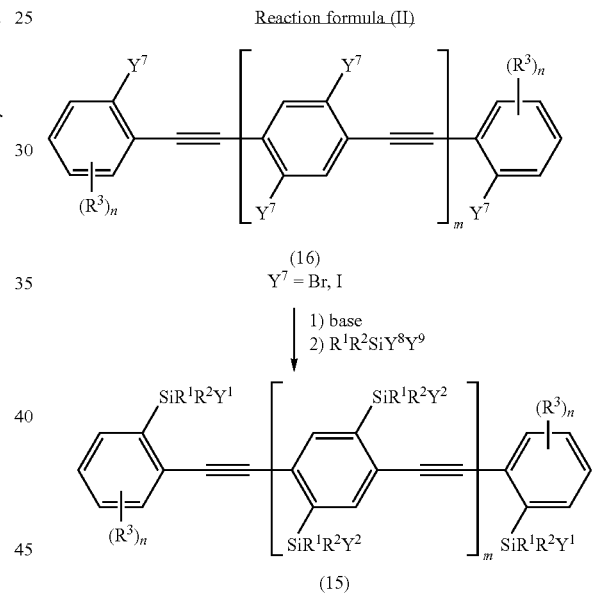

Cyclization products (condensed polycyclic π-conjugated organic materials) with silole rings in accordance with the present invention are of formula (1). The product is prepared, for example, by running an intramolecular reductive cyclization reaction between silicon and triple bond carbon. The reaction takes place as a straight-chain hydrocarbon is reacted with a metal reducing agent. The straight-chain hydrocarbon contains a triple bond and is either an aryl acetylene compound or a phenyl acetylene compound. The hydrocarbon, of formula (15), is composed of benzene rings with organic silicon as substituents. The straight-chain hydrocarbon may be a polyyne with 2 or more triple bonds.

Next will be described an example of synthesis producing the compound of formula (15). The raw material of formula (16) is made into a polymetal through a halogen/metal exchange reaction using an organic metal base as shown in reaction formula (II). The product is then collected with an organic silicon reagent of a general formula, $R^1R^2SiY^8Y^9$, to complete the synthesis of the compound of formula (15).

The organic metal base used may be, for example, an organic lithium reagent, such as n-BuLi, s-BuLi, and t-BuLi; or an organic magnesium reagent, such as alkyl Grignard reagent and alkyl magnesium amide. Among these examples, metalization in THF as a solvent using tert-BuLi (t-BuLi) results in the best yield.

In the organic silicon reagent $R^1R^2SiY^8Y^9$, each of $Y^8$ and $Y^9$, independent from the other, is a hydrogen atom, a halogen atom, an alkoxy group, an alkylthio group, an aryloxy group, an arylthio group, a silyl group, a substituted silyl group, a stannyl group, or a substituted stannyl group.

In formula (15), hydrogen atoms and alkoxy groups are particularly useful as $Y^1$, $Y^2$. If at least one of $Y^1$ and $Y^2$ is a hydrogen atom, for example, $R^1R^2SiH_2$ and $R^1R^2SiHCl$ are available as the organic silicon reagent $R^1R^2SiY^8Y^9$ for use in the synthesis. If $Y^1$ and $Y^2$ are alkoxy groups, $R^1R^2Si(OR)_2$ and $R^1R^2SiCl(NR_2)$ are available as the organic silicon reagent $R^1R^2SiY^8Y^9$ for use in the synthesis. In the latter event, the raw material of formula (16) is at first reacted with $R^1R^2SiCl(NR_2)$. The reactant is reacted with alcohol in the presence of an ammonium chloride or other acid catalyst without isolation, producing the target product.

Subsequently, the intramolecular reductive cyclization reaction will be described in reference to reaction formula (III) below. Reacting a compound of formula (15) with a metal reducing agent allows the intramolecular reductive cyclization reaction to proceed to yield a cyclization product of formula (1).

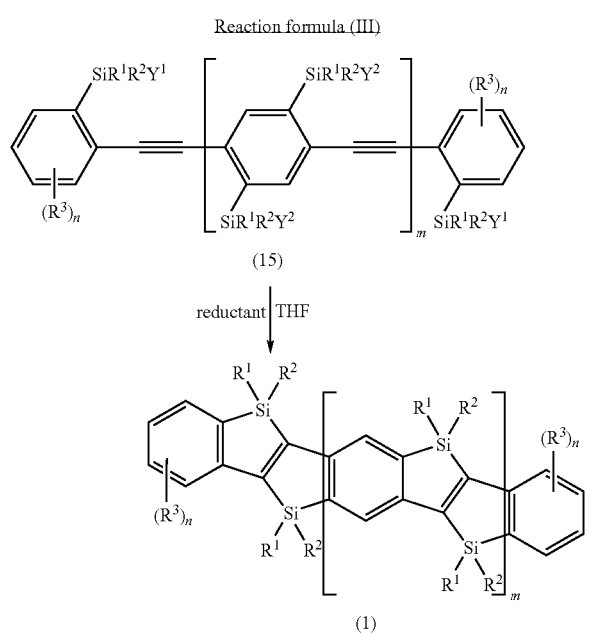

Examples of the metal reducing agent include lithium, lithium naphthalenide, lithium biphenylide, lithium(4,4'-di-tert-butylbiphenylide), lithium[8-(N,N-dimethylamino) naphthalenide], lithium/liquid ammonia, sodium, sodium naphthalenide, sodium biphenylide, sodium(4,4'-di-tert-butylbiphenylide), sodium[8-(N,N-dimethylamino)naphthalenide], sodium/liquid ammonia, potassium, and potassium graphite.

Examples of the solvent include THF as well as ether-based solvents, such as diethylether, dimethylether, and 1,2-dimethoxy ethane. The reaction temperature is from −78° C. to +50° C., preferably from −20° C. to +30° C.

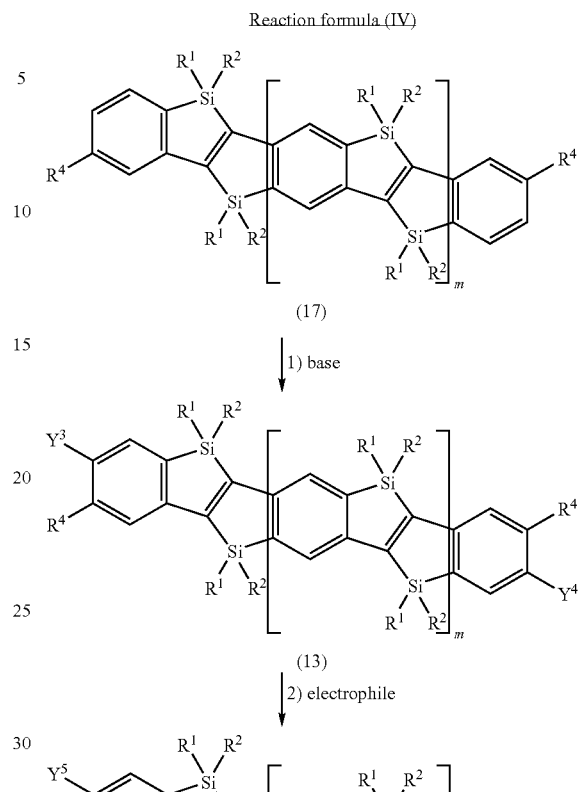

Next, the synthesis of the intermediate products of formula (14) will be described in reference to reaction formula (IV). A compound of formula (1) which contains the structure of formula (17) is used as a raw material. This material is processed using an organic metal base for ortho metalization. The metalization product is then transformed to a dimetalization product of formula (13). The product is processed using either an electrophilic halogenation agent or an electrophilic metalization agent to synthesize the compound of formula (14). See reaction formula (IV).

The organic metal base reagent used in the above process may be, for example, an organic lithium reagent, such as n-BuLi, s-BuLi, or t-BuLi; an organic magnesium reagent, such as alkyl magnesium amide; a zinc ate complex, such as Li[t-Bu$_2$ZnTMP] (TMP: 2,2,6,6-tetramethyl piperidine); or an n-BuLi/tert-BuOK mix reagent. Among these examples, sec-BuLi produces the best yield in metalization in THF.

The electrophilic halogenation agent may be, for example, ICH$_2$CH$_2$I, I$_2$, Br$_2$, ICl, NIS, NBS, BrCH$_2$CH2Br, BrCl$_2$CCCl$_2$Br, or BrF$_2$CCF$_2$Br.

The electrophilic metalization agent may be, for example, Me$_3$SnCl, Bu$_3$SnCl, Ph$_3$SnCl, R$^3$SiCl, R$^2$Si(OR)Cl, RSi(OR)$_2$Cl, Si(OR)$_3$Cl, R$_2$SiF$_2$, RSiF$_3$, B(OR)$_3$, (iPrO)B(—

OCH$_2$CMe$_2$CMe$_2$CH$_2$O—), ClB(NR$_2$)$_2$, MgCl$_2$, MgBr$_2$, MgI$_2$, ZnCl$_2$, ZnBr$_2$, ZnI$_2$, or ZnCl$_2$ (tmen). Note that R is an alkyl group.

Now, the synthesis of the polymer compound (polymer) containing repeating units of formula (4) will be described.

A derivative containing a functional group of formula (13) or formula (14) can be synthesized into a homopolymer by nickel catalyst homo coupling. Copolymer of those monomers of formulae (7) to (12) can be synthesized through one of transition-metal-catalyst cross coupling reactions, such as Kumada-Tamao coupling reaction, Negishi reaction, Kosugi-Migida-Stille reaction, Suzuki-Miyaura reaction, Sonogashira-Hagihara reaction, and Mizorogi-Heck reaction.

The following will describe the present invention in more detail by way of examples, which is by no means limiting the present invention.

EXAMPLE 1

Synthesis schemes for example 1 will be shown in reference to reaction formula (V).

First, taking bis[2-(ethoxydimethylsilyl)-5-(methoxy)phenyl]acetylene (2ba) as an example of the raw material compound of formula (15), its synthesis method will be described in reference to reaction formula (V) below.

An n-butyl lithium/hexane solution (1.6 M, 18.6 mL, 29.8 mmol) was added dropwise to a diethylether solution (280 mL) of the compound 1b (5.50 g, 13.9 mmol) at −35° C. The mixture was stirred for 4 hours while being kept at −30° C. to −25° C. Then, (N,N-diethylamino)dimethylchlorosilane (5.0 g, 30.2 mmol) was added dropwise to the reaction solution over 5 minutes at −25° C.

After the dropwise addition was completed, the mixture was stirred for 12 hours while slowly raising the temperature of the reaction mixture to room temperature. Thereafter, ethyl alcohol (3.7 mL, 63.4 mmol) and ammonium chloride (0.40 g, 7.5 mmol) were added, followed by stirring for another 23 hours at room temperature. The reaction solution was filtered to remove insolubles. The filtered solution was concentrated under reduced pressure.

The resultant mixture was purified by Florisil column chromatography (100 to 200 mesh, 5/1 hexane/AcOEt). The target product 2ba (5.85 g, 13.2 mmol) was thus obtained as a white solid at a yield of 95%.

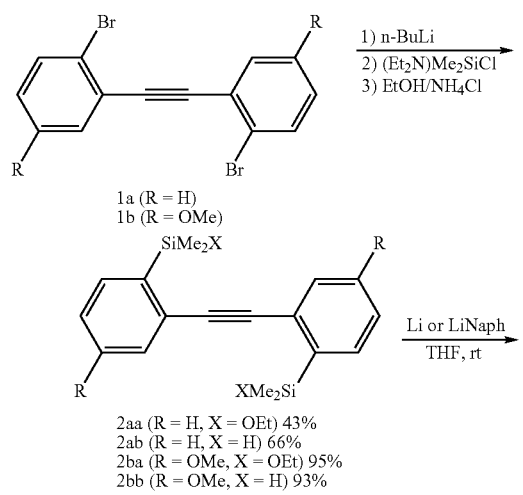

Physical property values of the obtained target product 2ba were measured by $^1$H NMR, $^{13}$C NMR, and $^{29}$Si NMR. Results are shown below.

$^1$H NMR (CDCl$_3$): δ 0.48 (s, 12H), 1.20-1.24 (m, 6H), 3.72 to 3.79 (m, 4H), 3.82 (s, 6H), 6.90 (dd, J=2.4 and 6.0 Hz, 2H), 7.12 (d, J=2.4 Hz, 2H), 7.56 (d, J=8.4 Hz, 2H). $^{13}$C NMR (CDCl$_3$): δ 0.72, 18.67, 55.15, 58.75, 92.73, 113.66, 117.38, 129.26, 131.60, 135.88, 160.21. $^{29}$Si NMR (CDCl$_3$): δ 6.46. Anal. Calcd for C$_{24}$H$_{34}$O$_4$Si$_2$: C, 65.11; H, 7.74. Found: C, 65.37; H, 7.79.

Next will be described bis[2-(ethoxydimethylsilyl)phenyl]acetylene (2aa) as another synthetic example of reaction formula (V).

The compound 2aa was obtained by a similar synthesis to the compound 2ba. The yield was 43%.

Physical property values of the resultant target product 2aa were measured by $^1$H NMR, $^{13}$C NMR, and $^{29}$Si NMR. Results are shown below.

$^1$H NMR (CDCl$_3$): δ 0.52 (s, 12H), 1.21-1.25 (m, 6H), 3.75-3.82 (m, 4H), 7.33-7.40 (m, 4H), 7.53-7.58 (m, 2H), 7.65-7.68 (m, 2H). $^{13}$C NMR (CDCl$_3$): δ −0.88, 18.62, 58.87, 93.19, 127.37, 127.98, 129.28, 131.90, 134.26, 140.42. $^{29}$Si NMR (CDCl$_3$): δ 6.59.

Next will be described bis[2-(dimethylsilyl)-5-(methoxy)phenyl]acetylene (2bb) as still another example of reaction formula (V).

An n-butyl lithium/hexane solution (1.6 M, 9.7 mL, 15.52 mmol) was added dropwise to a diethylether solution (145 mL) of the compound 1b (2.87 g, 7.25 mmol) at −35° C. The reaction solution was stirred for 4 hours while being kept between −30° C. to −25° C. Then, dimethylchlorosilane (2.5

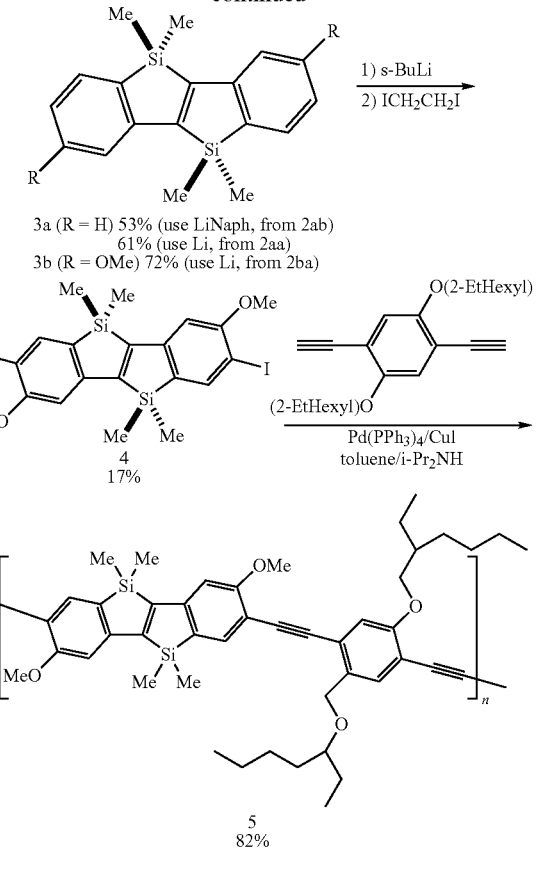

mL, 22.5 mmol) was added at −78° C. The mixture was stirred for 3 hours while slowly raising the temperature of the reaction mixture to room temperature.

After removing insolubles by filtering, the filtered solution was concentrated under reduced pressure to obtain the target product 2bb (2.38 g, 6.71 mmol) as a white solid at a yield of 93%. Physical property values of the resultant target product 2bb were measured by $^1$H NMR, $^{13}$C NMR, and $^{29}$Si NMR. Results are shown below.

$^1$H NMR (CDCl$_3$): δ 0.42 (d, J=3.9 Hz, 12H), 3.82 (s, 6H), 4.59 (m, 2H), 6.89 (dd, J=2.4 and 8.1 Hz, 2H), 7.08 (d, J=2.7 Hz, 2H), 7.46 (d, J=8.1 Hz, 2H). $^{13}$C NMR (CDCl$_3$): δ −3.42, 55.18, 92.45, 113.79, 117.22, 129.90, 130.91, 136.11, 160.18. $^{29}$Si NMR (CDCl$_3$): δ −17.38. Anal. Calcd for C$_{20}$H$_{26}$O$_2$Si$_2$: C, 67.74; H, 7.39. Found: C, 67.47; H, 7.25.

Next will be described bis[2-(dimethylsilyl)phenyl]acetylene (2ab) as yet another example of reaction formula (V). The compound 2ab was synthesized by a similar technique to the compound 2bb at a yield of 66%.

$^1$H NMR (CDCl$_3$): δ 0.46 (d, J=3.9 Hz, 12H), 4.59 (m, 2H), 7.30-7.40 (m, 4H), 7.53-7.58 (m, 4H). $^{13}$C NMR (CDCl$_3$): δ −3.65, 92.88, 127.50, 128.75, 129.15, 131.62, 134.63, 139.78. $^{29}$Si NMR (CDCl$_3$): δ −16.58. Anal. Calcd for C$_{18}$H$_{22}$Si$_2$: C, 73.40; H, 7.53. Found: C, 73.40; H, 7.53.

Now, referring to reaction formula (V), an example will be described in which 2,7-dimethoxy-5,5,10,10-tetramethyl-5,10-disila-5,10-dihydroindeno[2,1-a]indene (3b) was obtained. The target product 3b is an organic material in accordance with the present invention.

First, THF (85 mL) was added to a mixture of the compound 2ba (0.92 g, 2.07 mmol) and lithium (0.06 g, 8.7 mmol). The mixture was stirred for 5 hours at room temperature. Water was then added to the reaction mixture. The product was subjected to extraction using diethylether. The resultant ether layer, which was an organic layer, was dried with anhydrous magnesium sulfate and filtered to remove the drying agent. The filtered solution was then concentrated under reduced pressure.

Thereafter, the concentrate was purified by silica gel column chromatography. The purified product was recrystallized from hexane to obtain 0.53 g (1.50 mmol) of the target product 3b in the form of a colorless crystal at a yield of 72%.

$^1$H NMR (CDCl$_3$): δ 0.43 (s, 12H), 3.84 (s, 6H), 6.74 (dd, J=2.4 and 7.8 Hz, 2H), 6.85 (d, J=2.4 Hz, 2H), 7.47 (d, J=7.8 Hz, 2H). $^{13}$C NMR (CDCl$_3$): δ −3.14, 55.25, 110.21, 112.28, 131.19, 132.98, 151.30, 161.46, 164.79. $^{29}$Si NMR (CDCl$_3$): δ −1.78. Anal. Calcd for C$_{20}$H$_{24}$O$_2$Si$_2$: C, 68.13; H, 6.86. Found: C, 67.97; H, 6.86.

Now, referring to reaction formula (V), an example will be described in which 5,5,10,10-tetramethyl-5,10-disila-5,10-dihydroindeno[2, 1-a]indene (3a) was obtained. The target product 3a is an organic material in accordance with the present invention and was obtained by an intramolecular reductive cyclization reaction with lithium naphthalenide acting as a reducing agent for a derivative for bis(silylphenyl) acetylene.

First, a THF solution (15 mL) of lithium (132 mg, 19.03 mmol) and naphthalene (2.44 g, 19.04 mmol) was stirred for 4 hours at room temperature to prepare lithium naphthalenide. A THF solution (10 mL) of the compound 2ab (1.40 g, 4.75 mmol) was added to this solution at room temperature. Thereafter, the mixture was continuously stirred for 10 hours.

The solvent was distilled under reduced pressure. After that, chloroform was added to the resultant mixture. The mixture was then filtered to remove insolubles. The filtered solution was concentrated under reduced pressure and purified by silica gel column chromatography (hexane), to obtain 0.87 g of crude product. Further, the crude product was recrystallized from hexane to obtain 0.73 g (2.51 mmol) of the target product 3a in the form of a colorless crystal at a yield of 53%.

The compound 3a is synthesized also from the compound 2aa with the technique for the synthesis of the compound 3b. The yield was 61%.

$^1$H NMR (CDCl$_3$): δ 0.45 (s, 12H), 7.17-7.39 (m, 6H), 7.54-7.57 (m, 2H). $^{13}$C NMR (CDCl$_3$): δ −3.42, 124.65, 126.23, 129.94, 132.06, 140.48, 149.42, 163.67. $^{29}$Si NMR (CDCl$_3$): δ −0.75. Anal. Calcd for C$_{18}$H$_{20}$Si$_2$: C, 73.91; H) 6.89. Found: C, 73.72; H, 6.86.

Subsequently, referring to reaction formula (V), an example will be described in which 2,7-diiodo-3,8-dimethoxy-5,5,10,10-tetramethyl-5,10-disila-disila-5,10-dihydroindeno[2,1-a]indene (4) was obtained as an organic material in accordance with the present invention.

First, sec-butyl lithium/cyclohexane/hexane solution (0.98 M, 2.4 mL, 2.35 mmol) was added dropwise to a THF solution (7 mL) of the compound 3b (0.20 g, 0.57 mmol) at −78° C.

The solution was stirred for 8 hours while gradually raising the temperature of the solution from −78° C. to −25° C. Then, a THF (5 mL) solution of 1,2-diiodoethane (0.67 g, 2.4 mmol) was added dropwise to the reaction solution over 5 minutes, after which the mixture was stirred for 30 minutes.

A saturated aqueous solution of sodium thiosulfate was then added to the reaction mixture. The product was subjected to extraction using chloroform. The resultant organic layer was washed in a saturated saline solution and dried with anhydrous magnesium sulfate.

After removing the drying agent by filtering, the filtered solution was then concentrated under reduced pressure. The resultant mixture was washed in heated hexane. The obtained solid, or insolubles, was recrystallized from benzene to obtain 47.2 mg (0.78 mmol) of the target product 4 in the form of pale yellow powder at a yield of 17%.

$^1$H NMR (CDCl$_3$): δ 0.44 (s, 12H), 3.92 (s, 6H), 6.72 (s, 2H), 7.89 (s, 2H,). $^{13}$C NMR (CDCl$_3$): δ −3.24, 56.18, 84.39, 108.30, 133.70, 142.39, 151.31, 159.59, 164.34. $^{29}$Si NMR (CDCl$_3$): δ −0.80.

Subsequently, referring to reaction formula (V), an example synthesis will be described for poly{(3,8-dimethoxy-5,5,10,10-tetramethyl-5,10-disila-5,10-dihydroindeno[2,1-a]indene-3,7-diyl)-co-[2,5-bis(2-ethylhexiloxy)benzene-1,4-diethynyl]} (5). The target product 5 is a copolymer as an organic material in accordance with the present invention containing 5,10-disila-disila-5,10-dihydroindeno[2,1-a]indene as structural units.

First, a mixed 3/1 toluene/diisopropylamine (3.5 mL) solution of the compound 4 (50 mg, 0.084 mmol), 1,4-bis(2-ethylhexiloxy)-2,5-diethynylbenzene (32 mg, 0.084 mmol), tetrakis(triphenylphosphine)palladium (0) (9.7 mg, 8.4 mmol), and copper iodide (3.3 mg, 17.22 mmol) was stirred for 48 hours while being heated at 60° C.

Water was added to the reaction mixture. The resultant mixture was subjected to extraction using chloroform. The obtained organic layer was washed in an 5% aqueous solution of NH$_4$OH and a saturated saline solution, and then dried with magnesium sulfate.

After removing the drying agent by filtering, the filtered solution was then concentrated under reduced pressure. The concentrate was dissolved again in a small amount of chloroform and re-precipitated in methanol, to obtain 50 mg of the target product 5 in the form of yellow powder at a yield of 82%.

¹H NMR (CDCl₃): δ 0.47 (s, 12H), 0.89-0.99 (br m, 12H), 1.34 (br m, 16H), 1.80 (br m, 2H,), 3.98 (br m, 10H), 6.82 (s, 2H), 7.04 (s, 2H), 7.67 (s, 2H). The average polystyrene-equivalent molecular weight (Mn) determined by GPC was 37,500.

EXAMPLE 2

The following will describe other synthetic examples based on reaction formula (VI) below.

First, a method of synthesis from 1,4-bis[(2-bromophenyl)ethynyl]-2,5-dibromobenzene (6) as a raw material will be described.

A 3/1 toluene/triethylamine (9 mL) solution of 2-bromo-1-ethynylbenzene (90 mg, 4.98 mmol) was added to a mixed 3/1 toluene/triethylamine (12 mL) solution of 1,4-dibromo-2,5-diiodobenzene (1.15 g, 2.35 mmol) dichlorobis(triphenylphosphine)palladium (II) (33 mg, 47 mmol), and copper iodide (18 mg, 95 mmol) at room temperature and stirred for 12 hours at room temperature.

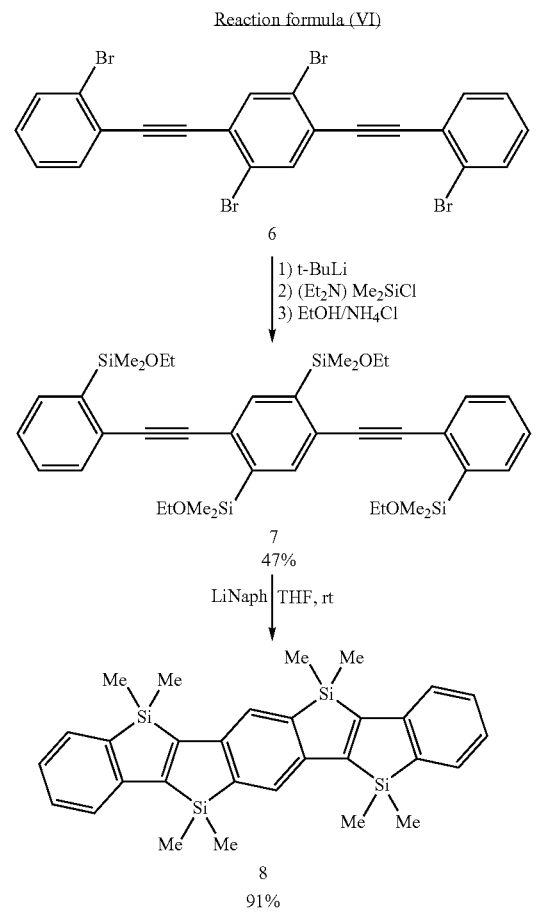

Reaction formula (VI)

A 1N aqueous solution of hydrochloric acid was added to the reaction mixture. The mixture was then subjected to extraction using methylene chloride. The obtained organic layer was washed in a saturated saline solution and dried with anhydrous magnesium sulfate. After removing the drying agent by filtering, the filtered solution was concentrated under reduced pressure. The resultant mixture was recrystallized from benzene, to obtain 1.17 g (1.97 mmol) of the target product 6 in the form of a white solid at a yield of 84%.

¹H NMR (CDCl₃): δ 7.20-7.35 (m, 4H), 7.59-7.65 (m, 4H), 7.83 (s, 2H). ¹³C NMR (CDCl₃): δ 90.81, 95.00, 123.57, 124.47, 125.59, 126.40, 127.02, 130.15, 132.54, 133.66, 136.34. Anal. Calcd for C₂₂H₁₀Br₄: C, 44.49; H, 1.70. Found: C, 44.42; H, 1.54.

Next will be described an example of synthesis for 2,5-bis{[2-(ethoxydimethysilyl)phenyl]ethynyl}-1,4-bis(ethoxydimethylsilyl)benzene (7) as an intermediate product using the compound 6.

First, a tert-butyl lithium/pentane solution (1.6 M, 4.3 mL, 6.88 mmol) was added dropwise to a THF solution (35 mL) of the compound 6 (0.50 g, 0.85 mmol) at −78° C. and stirred for 2 hours at −78° C. (N,N-diethylamino)dimethylchlorosilane (1.3 g, 7.84 mmol) was added to the reaction mixture. The mixture was then stirred over 10 hours while raising the temperature of the mixture to room temperature.

Thereafter, ethyl alcohol (1 mL, 17.13 mmol) and ammonium chloride (23 mg, 0.43 mmol) were added. The mixture was stirred for 14 hours at room temperature. After concentrating the reaction mixture under reduced pressure, diethylether was added. Insolubles removed by filtering.

The filtered solution was concentrated under reduced pressure and purified by silica gel column chromatography (5/1 hexane/EtOAc). The obtained crude product was further fractionated by GPC (chloroform), to obtain 272 mg (0.40 mmol) of the objective compound 7 in the form of a pale yellow color solid at a yield of 47%.

¹H NMR (CDCl₃): δ 0.53 (d, J=1.8 Hz, 24H), 1.22-1.27 (m, 12H), 3.76-3.83 (m, 8H), 7.32-7.41 (m, 4H), 7.56 (m, 2H), 7.68 (m, 2H), 7.85 (s, 2H). ¹³C NMR (CDCl₃): δ −1.03, −0.85, 18.67, 58.87, 58.95, 93.42, 94.90, 126.76, 127.50, 127.80, 129.28, 131.96, 134.28, 137.65, 140.63, 141.39. ²⁹Si NMR (CDCl₃): δ 6.29, 6.36.

Next will be described an example of synthesis for 5,7,12,14-tetrasila-diindeno[3,2-b:3,2-h](1,5-dihydro-s-indacene) (8) as an organic material in accordance with the present invention using the compound 7.

A THF solution (20 mL) of lithium (81.2 mg, 11.70 mmol) and naphthalene (1.50 g, 11.74 mmol) was stirred for 4 hours at room temperature to prepare lithium naphthalenide. A THF solution (6 mL) of the compound 7 (1.00 g, 1.46 mmol) was added to this solution at room temperature. The mixture was stirred for 5 hours.

A iodine/THF solution and subsequently a saturated aqueous solution of sodium thiosulfate were, added to the stirred solution. The mixture was then subjected to extraction using ether. The obtained ether layer was washed in an aqueous solution of 1N HCl and then in a saturated saline solution, followed by drying with sodium sulfate.

The reaction mixture of the ether layer was concentrated under reduced pressure and then purified by silica gel column chromatography (5/1 hexane/EtOAc), to obtain 0.68 g (1.33 mmol) of the target product 8 in the form of a yellow color solid at a yield of 91%.

1H NMR (CDCl₃): δ 0.49 (d, J=3.3 Hz, 24H), 7.18-7.39 (m, 4H), 7.47 (s, 2H), 7.57 (m, 2H). ¹³C NMR (CDCl₃): δ −3.35, −3.30, 124.52, 126.12, 128.39, 129.97, 132.04, 140.48, 142.99, 148.04, 149.62, 163.00, 163.80. ²⁹Si NMR (CDCl₃): δ −0.90, −0.60. Anal. Calcd for C₃₀H₃₄Si₄: C, 71.08; H, 6.76. Found: C, 71.31; H, 6.78.

Subsequently, optical properties of the compound 3a and the compound 8 were examined. A UV-visible absorption spectrum in THF showed a local maximum absorbed wavelength of 360 nm and 424 nm for the compound 3a and the compound 8 respectively.

A fluorescence spectrum showed extremely strong fluorescence for both of the compounds. The compound 3a and the compound 8 emit blue and verditer blue light with a local maximum fluorescence wavelength at 426 nm and 473 nm respectively. These results demonstrate that the compounds can be both used as an organic light-emitting material.

The absorbed and local maximum fluorescence wavelengths of the compound 3a are longer than those of similarly structured 5,10-dihydroindeno[2,1-a]indene by as much as 37 nm and 64 nm respectively.

A condensed polycyclic π-conjugated material in accordance with the present invention, to address the issue, is characterized in that it contains the compound of formula (1):

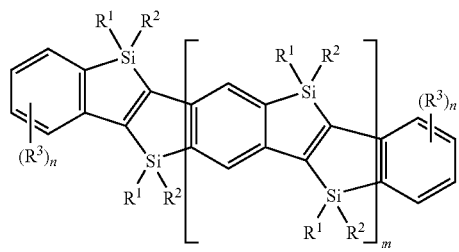

(1)

where each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^3$ is a hydrogen atom, an alkyl group, an alkylthio group, an arylalkyl group, an arylthio group, an arylalkylthio group, an arylalkenyl group, an arylalkynyl group, an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; m is from 1 to 50; and n is from 0 to 4.

According to the arrangement, the material is a planar, condensed polycyclic π-conjugated organic material prepared by condensing a benzene ring and a silole ring. The material therefore shows a good light emitting property, a high charge transport capability, and other advantages. The material is effective when used as an organic light-emitting material, organic charge transport material, etc. for EL displays.

The definition, "m is from 1 to 50," means that m may be set to any one of integers from 1 to 50. The definition, "n is from o to 4," means that n may be set to any one of integers from 0 to 4 and that when n is from 0 to 3, there are the same number of substituting hydrogen atoms in the benzene ring as a difference between n and 4.

The figures, m and n, have the same definition in chemical formulae below.

In the condensed polycyclic π-conjugated organic material, the compound may have formula (2):

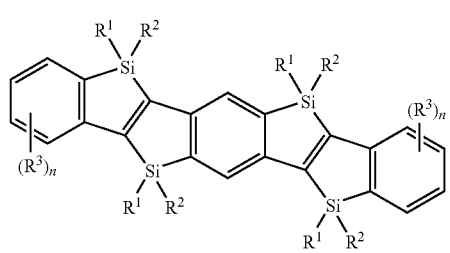

(2)

Another condensed polycyclic π-conjugated organic material in accordance with the present invention, to address the issue, is characterized in that it has formula (3):

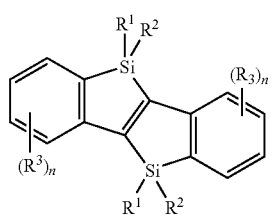

(3)

where each of $R^1$ and $R^2$, independent from the other, is a hydrogen atom, an alkyl group, an alkoxy group, an alkylthio group, an aryl group, an aryloxy group, an arylthio group, a arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^3$ is an alkyl group, an alkylthio group, an arylalkyl group, an arylthio group, an arylalkylthio group, an arylalkenyl group, an arylalkynyl group, an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; and n is from 1 to 4.

Still another condensed polycyclic π-conjugated organic material in accordance with the present invention, to address the issue, is characterized in that it is a polymer comprising a compound of formula (4) as a repeating unit and having a number average polystyrene-equivalent molecular weight of $10^3$ to $10^8$:

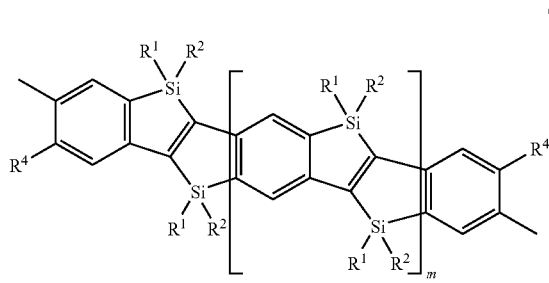

(4)

where each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^4$ is a substituent having ortho position activating effect, such as an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; and m is from 0 to 50.

According to the arrangement, the material is a planar, condensed polycyclic π-conjugated organic material prepared by condensing a benzene ring and a silole ring. The material therefore shows a good light emitting property, a high charge transport capability, and other advantages. The material is useful as an organic light-emitting material, organic charge transport material, etc. for EL displays. The material, being a polymer, also provides excellent moldability.

In the condensed polycyclic π-conjugated organic material, the compound may have formula (5):

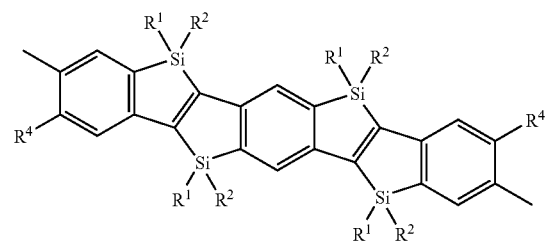

(5)

In the condensed polycyclic π-conjugated organic material, the compound may have formula (6):

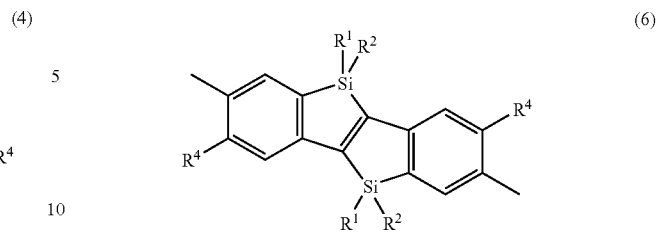

(6)

In the condensed polycyclic π-conjugated organic material, the polymer may further comprise at least one repeating unit selected from the group consisting of formulae (7), (8), (9), (10), (11), and (12):

 (7)

 (8)

 (9)

 (10)

 (11)

 (12)

where each of $Ar^1$, $Ar^2$, $Ar^3$, $Ar^4$, $Ar^5$, and $Ar^6$, independent from the others, is an arylene group, a divalent heterocyclic group, or a divalent group having a metal complex structure; each of $X^1$, $X^2$, $X^3$, $X^4$, and $X^5$, independent from the others, is —$CR^4$=$CR^5$—, —C≡C—, —N($R^6$)—, —B($R^7$)—, or —(Si$R^8 R^9$)q-; each of $R^4$ and $R^5$, independent from the other, is a hydrogen atom, an alkyl group, an aryl group, a monovalent heterocyclic group, a carboxyl group, a substituted carboxyl group, or a cyano group; each of $R^6$, $R^7$, $R^8$, and $R^9$, independent from the others, is a hydrogen atom, an alkyl group, an aryl group, a monovalent heterocyclic group, or an arylalkyl group; each of o, p, and q, independent from the others, is an integer from 1 to 12.

According to the arrangement, the polymer containing the compound of formula (4) as a repeating unit further contains one repeating unit selected from the group. This renders the wavelength of emitted light variable, while retaining the high light emitting efficiency of polymer.

An intermediate product for a condensed polycyclic π-conjugated organic material in accordance with the present invention, to address the issue, is characterized in that the intermediate product is a compound of:

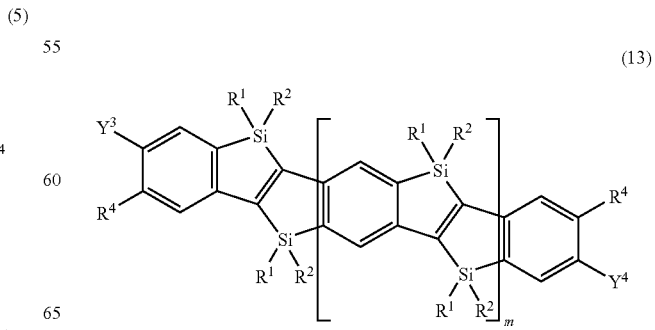

(13)

where each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^4$ is a substituent having ortho position activating effect, such as an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; m is from 0 to 50; each of $Y^3$ and $Y^4$, independent from the other, is lithium, potassium, sodium, magnesium halide, magnesium amide, or dialkyl zinc.

According to the arrangement, the inclusion of $R^4$ enables simpler and more reliable introduction of $Y_3$ and $Y_4$. A polymer with the aforementioned excellent properties can be obtained in a more stable manner. In the arrangement, $Y_3$ and $Y_4$ are bonded to the silicon-bonded carbon at a meta position. This straightens out the π-conjugated structure, thereby stabilizing emission of light, etc. In this case, it is desirable if $R^4$ is placed at a para position of the silicon-bonded carbon.

Another intermediate product for a condensed polycyclic π-conjugated organic material in accordance with the present invention, to address the issue, is characterized in that the intermediate product is a compound of:

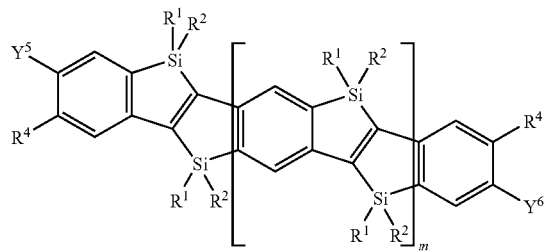

(14)

where each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^4$ is a substituent having ortho position activating effect, such as an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; m is from 0 to 50; each of $Y^5$ and $Y^6$, independent from the other, is a halogen atom, magnesium halide, alkyl magnesium, zinc halide, dialkyl zinc, a silyl group, a substituted silyl group, a stannyl group, a substituted stannyl group, boronic acid, or boronic ester.

According to the arrangement, the compound of formula (1), if having a structure of formula (4), can be transformed into a dimetalization product of formula (13) by ortho metalization. The compound of formula (14) can be derived from the product in a stable manner with good yield by further processing the product with an electrophilic halogenation agent or an electrophilic metalization agent.

A polymer compound (polymer) containing at least the compound of formula (4) as a repeating unit can be obtained in a stable manner with good yield through a coupling reaction between a derivative with a functional group of formula (13) or formula (14) (as a raw material) and such a derivative or another monomer of formula (7) to (12).

Still another intermediate product for a condensed polycyclic π-conjugated organic material in accordance with the present invention, to address the issue, is characterized in that the intermediate product is a compound of:

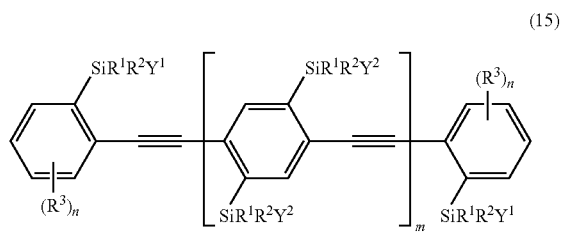

(15)

where each of $Y^1$ and $Y^2$, independent from the other, is a hydrogen atom, a halogen atom, an alkoxy group, an alkylthio group, an aryloxy group, an arylthio group, a silyl group, a substituted silyl group, a stannyl group, or a substituted stannyl group; each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^3$ is a hydrogen atom, an alkyl group, an alkylthio group, an arylalkyl group, an arylthio group, an arylalkylthio group, an arylalkenyl group, an arylalkynyl group, an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; m is from 0 to 50; and n is from 0 to 4.

According to the arrangement, a condensed polycyclic π-conjugated organic material and its polymer with the aforementioned excellent properties can be obtained in a more stable manner through an intramolecular reductive cyclization reaction. In the intermediate product, it is preferable if at least one $R^3$ is bonded at a para position with respect to the bonding position of the silicon bonded to the benzene ring to which that $R^3$ is bonded. This enables efficient production of an intermediate product (formula (13), formula (14), etc.) suitable for the synthesis of the polymer.

In the intermediate product, the silicon bonded to the benzene ring is preferable at an ortho position with respect to a bonding position with a triple bond carbon. This urges the intramolecular reductive cyclization reaction to proceed.

A method of manufacturing a condensed polycyclic π-conjugated organic material in accordance with the present invention, to address the issue, is characterized in that the method involves the steps of:

reacting a metal reducing agent with an aryl acetylene compound containing an organic silicon group; and allowing an intramolecular reductive cyclization reaction to proceed, so as to yield a compound of formula (1).

According to the method, a condensed polycyclic π-conjugated organic material and its intermediate product with the aforementioned excellent properties can be efficiently obtained through an intramolecular reductive cyclization reaction.

In the manufacture method, it is preferable if the aryl acetylene compound is a phenyl acetylene compound. According to the method, the aryl acetylene compound, when it is a phenyl acetylene compound, enables the intramolecular reductive cyclization reaction to proceed in a more stable manner.

The embodiments and examples described in Best Mode for Carrying Out the Invention are for illustrative purposes only and by no means limit the scope of the present invention. Variations are not to be regarded as a departure from the spirit and scope of the invention, and all such modifications as would be obvious to one skilled in the art are intended to be included within the scope of the claims below.

INDUSTRIAL APPLICABILITY

The condensed polycyclic π-conjugated organic material, its intermediate product, and method of manufacturing the condensed polycyclic π-conjugated organic material in accordance with the present invention, as described in the foregoing, are achieved by using as a hydrocarbon a benzene ring with organic silicon as a substituent, reacting a straight-chain hydrocarbon (aryl acetylene compound, phenyl acetylene compound) with a triple bond with a metal reducing agent, and allowing an intramolecular reductive cyclization reaction to proceed between silicon and the triple-bonded carbon.

The condensed polycyclic π-conjugated organic material in accordance with the present invention is a novel compound that can be used as a light-emitting material and a charge transport material.

In addition, the method of manufacturing a condensed polycyclic π-conjugated organic material in accordance with the present invention skips conventional special high temperature thermal decomposition reaction, and (i) is suited to mass-volume synthesis, (ii) enables the synthesis a derivative, containing a functional group, which is required in the synthesis of a polymer, and (iii) is applicable to the synthesis of a condensed polycyclic compound. The method can reliably ensures the manufacture of the aforementioned useful condensed polycyclic π-conjugated organic material.

The invention claimed is:

1. A condensed polycyclic π-conjugated organic material, being a polymer comprising a compound of formula (4) as a repeating unit and having a number average polystyrene-equivalent molecular weight of $10^3$ to $10^8$:

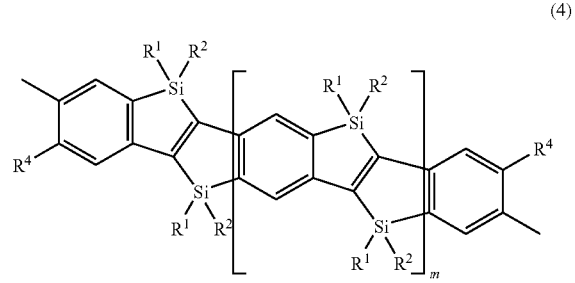

where each of $R^1$ and $R^2$, independent from the other, is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, a fluorinated alkyl group, or a halogen atom; $R^4$ is a substituent having ortho position activating effect, such as an alkoxy group, an aryloxy group, an arylalkoxy group, an amino group, a substituted amino group, a substituted silyl group, a substituted silyloxy group, a halogen atom, a trifluoromethyl group, a carbamoyl group, a substituted carbamoyl group, an imino group, a substituted imino group, an oxazoridyl group, an aminoalkyl group, an alkoxyalkyl group, a sulfo group, a substituted sulfo group, a substituted sulfamoyl group, a phosphoric ester group, a cyano group, an aryl group, or an ethynyl group; and m is from 0 to 50.

2. The condensed polycyclic π-conjugated organic material as set forth in claim 1, wherein the compound has formula (5):

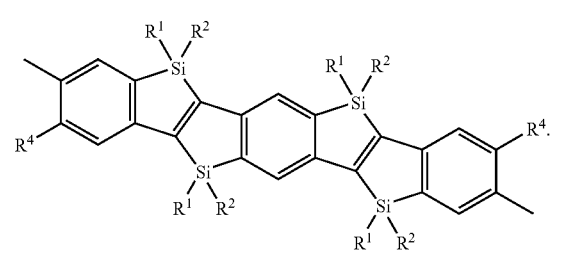

3. The condensed polycyclic π-conjugated organic material as set forth in claim 1, wherein the compound has formula (6):

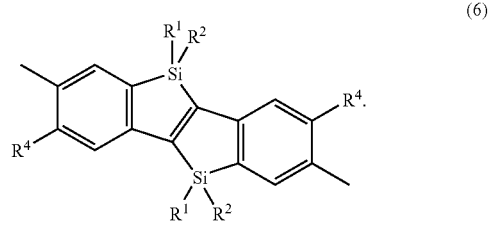

4. The condensed polycyclic π-conjugated organic material as set forth in claim 1, the polymer further comprising at least one repeating unit selected from the group consisting of formulae (7), (8), (9), (10), (11), and (12):

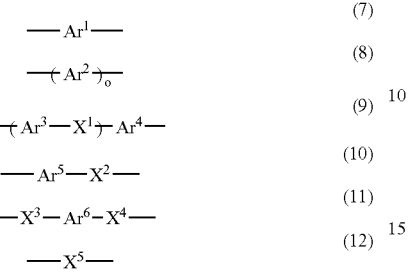

where each of $Ar^1$, $Ar^2$, $Ar^3$, $Ar^4$, $Ar^5$, and $Ar^6$, independent from the others, is an arylene group, a divalent heterocyclic group, or a divalent group having a metal complex structure; each of $X^1$, $X^2$, $X^3$, $X^4$, and $X^5$, independent from the others, is $-CR^4=CR^5-$, $-C\equiv C-$, $-N(R^6)-$, $-B(R^7)-$, or $-(SiR^8R^9)_q-$; each of $R^4$ and $R^5$, independent from the other, is a hydrogen atom, an alkyl group, an aryl group, a monovalent heterocyclic group, a carboxyl group, a substituted carboxyl group, or a cyano group; each of $R^6$, $R^7$, $R^8$, and $R^9$, independent from the others, is a hydrogen atom, an alkyl group, an aryl group, a monovalent heterocyclic group, or an arylalkyl group; each of o, p, and q, independent from the others, is an integer from 1 to 12.

* * * * *